United States Patent [19]

Miller et al.

[11] Patent Number: 5,780,497

[45] Date of Patent: Jul. 14, 1998

[54] 2-PHENYL-1-|4-(AMINO-1-YL-ALK-1-YNYL)-BENZYL|-1H-INDOL-5-OLS AS ESTROGENIC AGENTS

[75] Inventors: Chris P. Miller, Strafford; Michael D. Collini, Clifton Heights; Bach D. Tran, Media, all of Pa.

[73] Assignee: American Home Products Corporation, Madison, N.J.

[21] Appl. No.: 832,701

[22] Filed: Apr. 14, 1997

Related U.S. Application Data

[60] Provisional application No. 60/020,990 Apr. 19, 1996.

[51] Int. Cl.$^6$ .................. A61K 31/40; A61K 31/405; A61K 31/445; A61K 31/41; A61K 31/425; A61K 31/415; C07D 209/04; C07D 209/02

[52] U.S. Cl. .................. 514/414; 548/465; 548/483; 548/123; 548/124; 548/146; 548/202; 548/208; 548/214; 548/215; 548/235; 548/237; 548/240; 548/247; 548/312.1; 548/364.7; 548/511; 514/415; 514/323; 514/360; 514/365; 514/372; 514/374; 514/378; 514/397; 514/402; 514/406; 546/201

[58] Field of Search .................. 548/465, 483, 548/490, 491, 123, 124, 146, 202, 208, 214, 215, 235, 237, 240, 247, 312.1, 364.7, 511; 546/201; 514/414, 415, 323, 360, 365, 372, 374, 378, 397, 702, 406

[56] References Cited

U.S. PATENT DOCUMENTS

| | | | |
|---|---|---|---|
| 4,943,572 | 7/1990 | von Angerer | 514/253.2 |
| 5,023,254 | 6/1991 | von Angerer | 514/235.5 |
| 5,124,335 | 6/1992 | Patchett et al. | 514/300 |
| 5,496,844 | 3/1996 | Inai et al. | 514/415 |

FOREIGN PATENT DOCUMENTS

| | | |
|---|---|---|
| 0639567 | 2/1995 | European Pat. Off. |
| 9310741 | 6/1993 | WIPO |
| 9323374 | 11/1993 | WIPO |
| 9517383 | 6/1995 | WIPO |
| 9603375 | 2/1996 | WIPO |

OTHER PUBLICATIONS von Angerer et al., "2-Phenylindoles," J. Med. Chem. 1987, 30, 131–136.

von Angerer et al., "1-(Aminoalkyl)-2-phenylindoles as Novel Pure Estrogen Antagonists," J. Med. Chem. 1990, 33, 2635–2640.

Charles Rackley, M.D. "Contemporary Treatment of Lipid Abnormalities," Contemporary Treatments in Cardiovascular Disease, 1, 1996, 49–58.

Biberger et al., J. Steroid Biochem. Molec. Biol., vol. 58, No. 1, pp. 31–43, 1996.

von Angerer et al., Amer. Chem. Soc., pp. 132–136, 1986.

Henderson et al., Ann. N.Y. Aca. Sci., pp. 176, 177, 189, 1995.

Oparil "Hypertension in postmenopausal Woman:Pathology and Management" EMBASE 95:283951, 1995.

von Angerer et al., J. Med. Chem. vol. 27, pp. 1439–1447, 1984.

Biberger "2-Phenylindoles with Sulfer Containing Side Chains", CA 125:316191, 1996.

*Primary Examiner*—Mukund J. Sham
*Assistant Examiner*—Ann M. Kessinger
*Attorney, Agent, or Firm*—Steven R. Eck

[57] ABSTRACT

The present invention relates to new 2-Phenyl-1-|4-(amino-1-yl-alk-1-ynyl)benzyl|-1H-indol-5-ol compounds which are useful as estrogenic agents, as well as pharmaceutical compositions and methods of treatment utilizing these compounds, which have the general structure below.

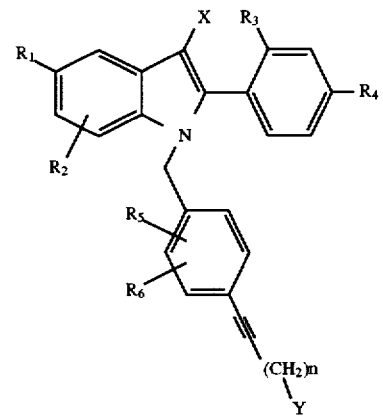

or

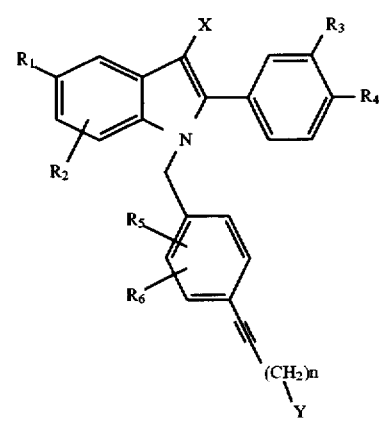

10 Claims, No Drawings

2-PHENYL-1-[4-(AMINO-1-YL-ALK-1-YNYL)-BENZYL]-1H-INDOL-5-OLS AS ESTROGENIC AGENTS

This application claims the benefit of U.S. Provisional Application Ser. No. 60/020,990, filed Apr. 19, 1996.

The present invention relates to new 2-Phenyl-1-[4-(amino-1-yl-alk-1-ynyl)benzyl]-1H-indol-5-ol compounds which are useful as estrogenic agents, as well as pharmaceutical compositions and methods of treatment utilizing these compounds.

BACKGROUND OF THE INVENTION

The use of hormone replacement therapy for bone loss prevention in post-menopausal women is well precedented. The normal protocol calls for estrogen supplementation using such formulations containing estrone, estriol, ethynyl estradiol or conjugated estrogens isolated from natural sources (i.e. Premarin® conjugated estrogens from Wyeth-Ayerst). In some patients, therapy may be contraindicated due to the proliferative effects of unopposed estrogens (estrogens not given in combination with progestins) have on uterine tissue. This proliferation is associated with increased risk for endometriosis and/or endometrial cancer. The effects of unopposed estrogens on breast tissue are less clear, but are of some concern. The need for estrogens which can maintain the bone sparing effect while minimizing the proliferative effects in the uterus and breast is evident. Certain nonsteroidal antiestrogens have been shown to maintain bone mass in the ovariectomized rat model as well as in human clinical trials. Tamoxifen (sold as Novadex® brand tamoxifen citrate by Zeneca Pharmaceuticals, Wilmington, Del.), for example, is a useful palliative for the treatment of breast cancer and has been demonstrated to exert an estrogen agonist-like effect on the bone, in humans. However, it is also a partial agonist in the uterus and this is cause for some concern. Raloxifene, a benzothiophene antiestrogen, has been shown to stimulate uterine growth in the ovariectomized rat to a lesser extent than Tamoxifen while maintaining the ability to spare bone. A suitable review of tissue selective estrogens is seen in the article "Tissue-Selective Actions Of Estrogen Analogs", Bone Vol. 17, No. 4, October 1995, 181S–190S.

The use of indoles as estrogen antagonists has been reported by Von Angerer, Chemical Abstracts, Vol. 99, No. 7 (1983), Abstract No. 53886u. Also, see, J. Med. Chem. 1990, 33, 2635–2640; J. Med. Chem. 1987, 30, 131–136. Also see Ger. Offen., DE 3821148 A1 891228 and WO 96/03375. These prior art compounds share structural similarities with the present compounds, but are functionally different. For compounds containing a basic amine, there is no phenyl group to rigidify the side chain.

WO A 95 17383 (Karo Bio AB) describes indole antiestrogens with long straight chains. Another related patent WO A 93 10741 describes 5-Hydroxyindoles with a broad range of side chains. WO 93/23374 (Otsuka Pharmaceuticals, Japan) describes compounds sharing structural similarities with those of the present invention, except with the structure referred to as $R_3$ in the present formulas I and II, below, is defined as thioalkyl and the reference discloses no such compounds having chains from the indole nitrogen having the same structure as the ones provided by the present invention.

DESCRIPTION OF THE INVENTION

The present invention provides 2-Phenylindoles of the general structures shown in formulas (I) and (II), below, which exhibit strong binding to the estrogen receptor and are estrogen agonists/antagonists useful for the treatment of diseases associated with estrogen deficiency. In vitro assays including an Ishikawa alkaline phoshatase assay and an ERE transfection assay show these compounds are antiestrogens with little to no intrinsic estrogenicity. In a three-day ovariectomized rat model, compounds of formula (I) are capable of antagonizing the effects of 17β-estradiol while showing little uterine stimulation when dosed alone.

The present invention includes compounds of formulas (I) or (II):

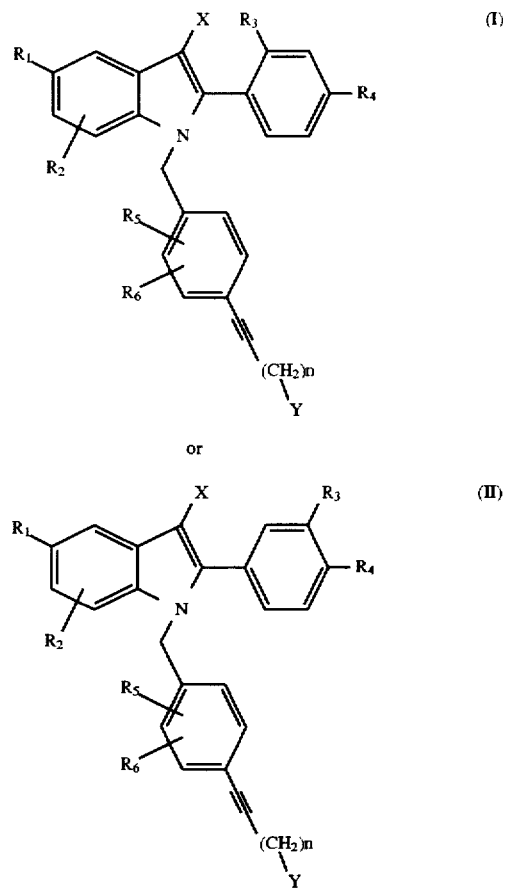

wherein:

$R_1$ is selected from H, OH or the $C_1$–$C_4$ esters or alkyl ethers thereof, or halogen;

$R_2$, $R_3$, $R_4$, $R_5$, and $R_6$ are independently selected from H, OH or the $C_1$–$C_4$ esters or alkyl ethers thereof, halogen, cyano, $C_1$–$C_6$ alkyl, or trifluoromethyl, with the proviso that, when $R_1$ is H, $R_2$ is not OH;

X is selected from H, $C_1$–$C_6$ alkyl, cyano, nitro, triflouromethyl, halogen;

n is 2 or 3;

Y is selected from:

a) the moiety:

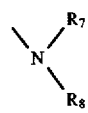

wherein $R_7$ and $R_8$ are independently selected from the group of H, $C_1$–$C_6$ alkyl, phenyl;

b) a five-membered saturated, unsaturated or partially unsaturated heterocycle containing up to two heteroatoms selected from the group consisting of —O—, —NH—, —N($C_1C_4$ alkyl)-, —N=, and —S(O)$_m$—, wherein m is an integer of from 0–2, optionally substituted with 1–3 substituents independently selected from the group consisting of hydrogen, hydroxyl, halo, $C_1$–$C_4$ alkyl, trihalomethyl, $C_1$–$C_4$ alkoxy, trihalomethoxy, $C_1$–$C_4$ acyloxy, $C_1$–$C_4$ alkylthio, $C_1$–$C_4$ alkylsulfinyl, $C_1$–$C_4$ alkylsulfonyl, hydroxy ($C_1$–$C_4$)alkyl, —$CO_2H$—, —CN—, —CONHR$_1$—, —$NH_2$—, $C_1$–$C_4$ alkylamino, $C_1$–$C_4$ dialkylamino, —$NHSO_2R_1$—, —NHCOR$_1$—, —$NO_2$—, and phenyl optionally substituted with 1–3 ($C_1$–$C_4$)alkyl;

c) a six-membered saturated, unsaturated or partially unsaturated heterocycle containing up to two heteroatoms selected from the group consisting of —O—, —NH—, —N($C_1C_4$ alkyl)-, —N=, and —S(O)$_m$—, wherein m is an integer of from 0–2, optionally substituted with 1–3 substituents independently selected from the group consisting of hydrogen, hydroxyl, halo, $C_1$–$C_4$ alkyl, trihalomethyl, $C_1$–$C_4$ alkoxy, trihalomethoxy, $C_1$–$C_4$ acyloxy, $C_1$–$C_4$ alkylthio, $C_1$–$C_4$ alkylsulfinyl, $C_1$–$C_4$ alkylsulfonyl, hydroxy ($C_1$–$C_4$)alkyl, —$CO_2H$—, —CN—, —CONHR$_1$—, —$NH_2$—, $C_1$–$C_4$ alkylamino, di($C_1$–$C_4$)alkylamino, —$NHSO_2R_1$—, —NHCOR$_1$—, —$NO_2$, and phenyl optionally substituted with 1–3 ($C_1$–$C_4$)alkyl;

d) a seven-membered saturated, unsaturated or partially unsaturated heterocycle containing up to two heteroatoms selected from the group consisting of —O—, —NH—, —N($C_1C_4$ alkyl)-, —N=, and —S(O)$_m$—, wherein m is an integer of from 0–2, optionally substituted with 1–3 substituents independently selected from the group consisting of hydrogen, hydroxyl, halo, $C_1$–$C_4$ alkyl, trihalomethyl, $C_1$–$C_4$ alkoxy, trihalomethoxy, $C_1$–$C_4$ acyloxy, $C_1$–$C_4$ alkylthio, $C_1$–$C_4$ alkylsulfinyl, $C_1$–$C_4$ alkylsulfonyl, hydroxy ($C_1$–$C_4$)alkyl, —$CO_2H$—, —CN—, —CONHR$_1$—, —$NH_2$—, $C_1$–$C_4$ alkylamino, di($C_1$–$C_4$)alkylamino, —$NHSO_2R_1$—, —NHCOR$_1$—, —$NO_2$, and phenyl optionally substituted with 1–3 ($C_1$–$C_4$)alkyl; or e) a bicyclic heterocycle containing from 6–12 carbon atoms either bridged or fused and containing up to two heteroatoms selected from the group consisting of —O—, —NH—, —N($C_1C_4$ alkyl)-, and —S(O)$_m$—, wherein m is an integer of from 0–2, optionally substituted with 1–3 substituents independently selected from the group consisting of hydrogen, hydroxyl, halo, $C_1$–$C_4$ alkyl, trihalomethyl, $C_1$–$C_4$ alkoxy, trihalomethoxy, $C_1$–$C_4$ acyloxy, $C_1$–$C_4$ alkylthio, $C_1$–$C_4$ alkylsulfinyl, $C_1$–$C_4$ alkylsulfonyl, hydroxy ($C_1$–$C_4$)alkyl, —$CO_2H$—, —CN—, —CONHR$_1$—, —$NH_2$—, $C_1$–$C_4$ alkylamino, di($C_1$–$C_4$)alkylamino, —$NHSO_2R_1$—, —NHCOR$_1$—, —$NO_2$, and phenyl optionally substituted with 1–3 ($C_1$–$C_4$)alkyl;

and the pharmaceutically acceptable salts thereof.

The more preferred compounds of this invention are those having the general structures I or II, above, wherein:

$R_1$ is selected from H, OH or the $C_1$–$C_4$ esters or alkyl ethers thereof, halogen;

$R_2$, $R_3$, $R_4$, $R_5$, and $R_6$ are independently selected from H, OH or the $C_1$–$C_4$ esters or alkyl ethers thereof, halogen, cyano, $C_1$–$C_6$ alkyl, or trifluoromethyl, with the proviso that, when $R_1$ is H, $R_2$ is not OH;

X is selected from H, $C_1$–$C_6$ alkyl, cyano, nitro, trifluoromethyl, halogen; p1 Y is the moiety

$R_7$ and $R_8$ are selected independently from H, $C_1$–$C_6$ alkyl, or combined by —(CH$_2$)p—, wherein p is an integer of from 2 to 6, so as to form a ring, the ring being optionally substituted by up to three substituents selected from the group of hydrogen, hydroxyl, halo, $C_1$–$C_4$ alkyl, trihalomethyl, $C_1$–$C_4$ alkoxy, trihalomethoxy, $C_1$–$C_4$ alkylthio, $C_1$–$C_4$ alkylsulfinyl, $C_1$–$C_4$ alkylsulfonyl, hydroxy ($C_1$–$C_4$)alkyl, —$CO_2H$, —CN, —CONH($C_1$–$C_4$)alkyl, —$NH_2$, $C_1$–$C_4$ alkylamino, $C_1$–$C_4$ dialkylamino, —$NHSO_2$($C_1$–$C_4$)alkyl, —NHCO($C_1$–$C_4$), and —$NO_2$;

and the pharmaceutically acceptable salts thereof.

The rings formed by a concatenated $R_7$ and $R_8$, mentioned above, may include, but are not limited to, aziridine, azetidine, pyrrolidine, piperidine, or hexamethyleneamine rings.

The most preferred compounds of the present invention are those having the structural formulas I or II, above, wherein $R_1$ is OH; $R_2$–$R_6$ are as defined above; X is selected from the group of Cl, $NO_2$, CN, $CF_3$, or $CH_3$; and Y is the moiety

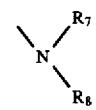

and $R_7$ and $R_8$ are concatenated together as —(CH$_2$)$_p$—, wherein p is an integer of from 4 to 6, to form a ring optionally substituted by up to three substituents selected from the group of hydrogen, hydroxyl, halo, $C_1$–$C_4$ alkyl, trihalomethyl, $C_1$–$C_4$ alkoxy, trihalomethoxy, $C_1$–$C_4$ alkylthio, $C_1$–$C_4$ alkylsulfinyl, $C_1$–$C_4$ alkylsulfonyl, hydroxy ($C_1$–$C_4$)alkyl, —$CO_2H$, —CN, —CONH($C_1$–$C_4$), —$NH_3$, $C_1$–$C_4$ alkylamino, $C_1$–$C_4$ dialkylamino, —$NHSO_2$($C_1$–$C_4$), —NHCO($C_1$–$C_4$), and —$NO_3$;

and the pharmaceutically acceptable salts thereof.

It is further preferred that, when $R_7$ and $R_8$ are concatenated together as —(CH$_2$)p—, the ring so formed is optionally substituted with 1–3 substituents selected from a group containing $C_1$–$C_3$ alkyl, trifluoromethyl, halogen, hydrogen, phenyl, nitro, —CN.

The invention includes acceptable salt forms formed from the addition reaction with either inorganic or organic acids. Inorganic acids such as hydrochloric acid, hydrobromic acid, hydroiodic acid, sulfuric acid, phosphoric acid, nitric acid useful as well as organic acids such as acetic acid, propionic acid, citric acid, maleic acid, malic acid, tartaric acid, phthalic acid, succinic acid, methanesulfonic acid, toluenesulfonic acid, napthalenesulfonic acid, camphorsulfonic acid, benzenesulfonic acid are useful. It is known that compounds possessing a basic nitrogen can be complexed with many different acids (both protic and not protic) and usually it is preferred to administer a compound of this invention in the form of an acid addition salt.

Compounds of this invention can be synthesized in a general sense according to Scheme 1.

Scheme 1

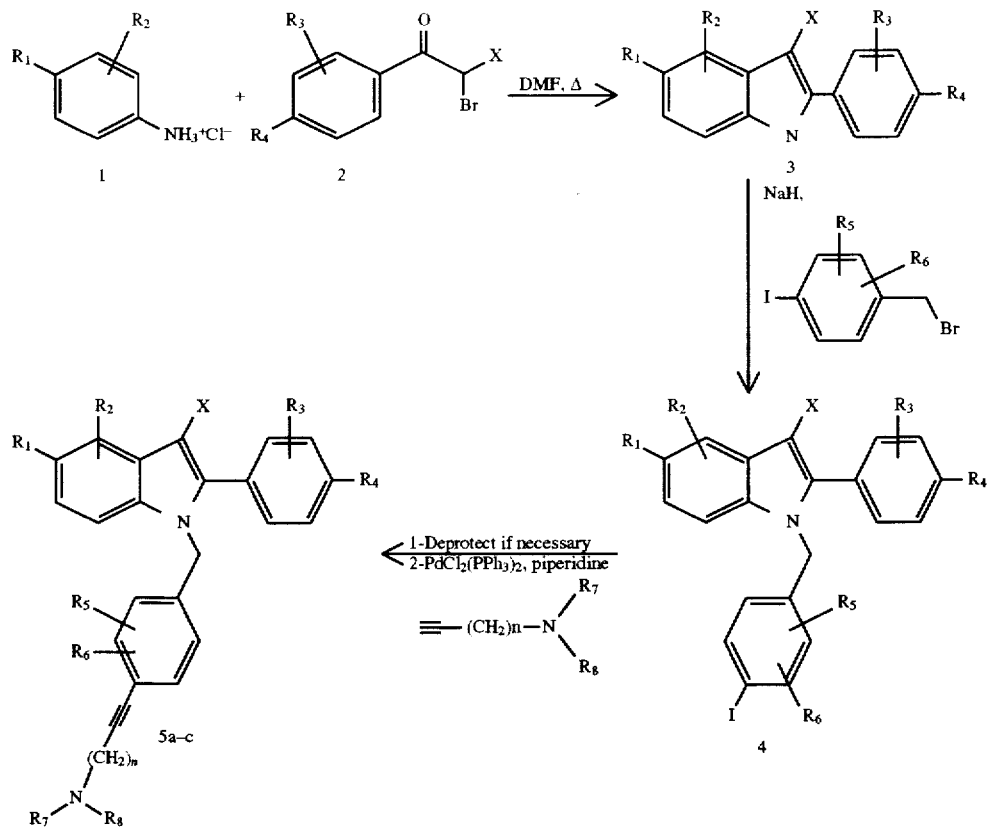

The initial indole synthesis may be accomplished by heating an appropriately substituted aniline (1) with an appropriately substituted alpha-bromophenylalkylphenone (2) in a suitably high boiling solvent such as DMF. The product is then alkylated with 4-iodobenzyl bromide to give the substituted indole (3). At this point, deprotection of phenols (if present) is done. Normally, the phenols are protected as benzyl ethers and can conveniently be cleaved with TMSI. The propargylamines can then be coupled to the phenyl iodide. The propargylamines are typically prepared from an alkynyl bromide or alkynyl tosylate by substitution with the appropriate amine. The substitution reaction is done in situ, without isolating the propargylamine. Compounds substituted at the 3-position with groups other then alkyl may be prepared by first preparing the indole substituted at the 3-position with —H. The indole can then be electrophilically halogenated, formylated, etc., to give other 3-substituted compounds.

The compounds of the invention are partial estrogen agonists and display high affinity for the estrogen receptor. Unlike many estrogens, however, these compounds do not cause increases in uterine wet weight. These compounds are antiestrogenic in the uterus and can completely antagonize the trophic effects of estrogen agonists in uterine tissue. These compounds are useful in treating or preventing mammal disease states or syndromes which are caused or associated with an estrogen deficiency.

The present compounds have the ability to behave like estrogen agonists by lowering cholesterol and preventing bone loss. Therefore, these compounds are useful for treating many maladies including osteoporosis, prostatic hypertrophy, infertility, breast cancer, endometrial cancer, cardiovascular disease, contraception, Alzheimer's disease and melanoma. Additionally, these compounds can be used for hormone replacement therapy in post-menopausal women or in other estrogen deficiency states where estrogen supplementation would be beneficial.

The compounds of this invention may also be used in methods of treatment for bone loss, which may result from an imbalance in a individual's formation of new bone tissues and the resorption of older tissues, leading to a net loss of bone. Such bone depletion results in a range of individuals, particularly in post-menopausal women, women who have undergone hysterectomy, those receiving or who have received extended corticosteroid therapies, those experiencing gonadal dysgenesis, and those suffering from Cushing's syndrome. Special needs for bone replacement can also be addressed using these compounds in individuals with bone fractures, defective bone structures, and those receiving bone-related surgeries and/or the implantation of prosthesis. In addition to those problems described above, these compounds can be used in treatments for osteoarthritis, Paget's disease, osteomalacia, osteohalisteresis, endometrial cancer, multiple myeloma and other forms of cancer having deleterious effects on bone tissues. Methods of treating the maladies listed herein are understood to comprise administering to an individual in need of such treatment a pharmaceutically effective amount of one or more of the compounds of this invention or a pharmaceutically acceptable salt thereof. This invention also includes pharmaceutical compositions utilizing one or more of the present compounds, and/or the pharmaceutically acceptable salts thereof, along with one or more pharmaceutically acceptable carriers, excipients, etc.

It is understood that the dosage, regimen and mode of administration of these compounds will vary according to the malady and the individual being treated and will be subjected to the judgment of the medical practitioner involved. It is preferred that the administration of one or more of the compounds herein begins at a low dose and be increased until the desired effects are achieved.

Effective administration of these compounds may be given at a dose of from about 0.1 mg/day to about 1,000 mg/day. Preferably, administration will be from about 50 mg/day to about 600 mg/day in a single dose or in two or more divided doses. Such doses may be administered in any manner useful in directing the active compounds herein to the recipient's bloodstream, including orally, parenterally (including intravenous, intraperitoneal and subcutaneous injections), and transdermally. For the purposes of this disclosure, transdermal administrations are understood to include all administrations across the surface of the body and the inner linings of bodily passages including epithelial and mucosal tissues. Such administrations may be carried out using the present compounds, or pharmaceutically acceptable salts thereof, in lotions, creams, foams, patches, suspensions, solutions, and suppositories (rectal and vaginal).

Oral formulations containing the active compounds of this invention may comprise any conventionally used oral forms, including tablets, capsules, buccal forms, troches, lozenges and oral liquids, suspensions or solutions. Capsules may contain mixtures of the active compound(s) with inert fillers and/or diluents such as the pharmaceutically acceptable starches (e.g. corn, potato or tapioca starch), sugars, artificial sweetening agents, powdered celluloses, such as crystalline and microcrystalline celluloses, flours, gelatins, gums, etc. Useful tablet formulations may be made by conventional compression, wet granulation or dry granulation methods and utilize pharmaceutically acceptable diluents, binding agents, lubricants, disintegrants, suspending or stabilizing agents, including, but not limited to, magnesium stearate, stearic acid, talc, sodium lauryl sulfate, microcrystalline cellulose, carboxymethylcellulose calcium, polyvinylpyrrolidone, gelatin, alginic acid, acacia gum, xanthan gum, sodium citrate, complex silicates, calcium carbonate, glycine, dextrin, sucrose, sorbitol, dicalcium phosphate, calcium sulfate, lactose, kaolin, mannitol, sodium chloride, talc, dry starches and powdered sugar. Oral formulations herein may utilize standard delay or time release formulations to alter the absorption of the active compound(s). Suppository formulations may be made from traditional materials, including cocoa butter, with or without the addition of waxes to alter the suppository's melting point, and glycerin. Water soluble suppository bases, such as polyethylene glycols of various molecular weights, may also be used.

Solvents used for the reactions described herein were anhydrous Aldrich Sure Seal™ without further purification. Reagents were typically Aldrich and used without further purification. All reactions were carried out under a nitrogen atmosphere. Chromatography was performed using 230–400 mesh silica gel (Merck Grade 60, Aldrich Chemical Company). Thin layer chromatography was performed with Silica Gel 60 $F_{254}$ plates from EM Science. $^1$H NMR spectra were obtained on a Bruker AM-400 instrument in DMSO and chemical shifts reported in ppm. Melting points were determined on a Thomas-Hoover apparatus and are uncorrected. IR spectra were recorded on a Perkin-Elmer 784 spectrophotometers. Mass spectra were recorded on a Kratos MS 50 or Finnigan 8230 mass spectrometers. Elemental analyses were obtained with a Perkin-Elmer 2400 elemental analyzer. Analysis values for compounds with CHN analysis reported were within 0.4% of theoretical values.

The present invention is further illustrated by the following non-limiting examples.

EXAMPLE 1

5-Benzyloxy-2-(4-benzyloxy-phenyl)-3-methyl-1H-indole

A flask was charged with 4-benzyloxyaniline (45 g, 0.23 mol), 4'-benzyloxy-2-bromophenylpropiophenone (21 g, 0.066 mol), and DMF (50 mL). The reaction was heated at reflux for 30 minutes and then cooled to rt and then partitioned between EtOAc (250 mL) and 1N HCl (aq) (100 mL). The EtOAc was washed with NaHCO$_3$ (aq) and brine, dried over MgSO$_4$. The solution was concentrated and the residue taken up in CH$_2$Cl$_2$ and hexanes added to precipitate out 25 g of a crude solid. The solid was dissolved in CH$_2$Cl$_2$ and evaporated onto silica gel and chromatographed using CH$_2$Cl$_2$/Hexane (1:5) to yield 9.2 g of a tan solid (33%): Mpt=150°–152° C.; $^1$H NMR (DMSO) 10.88 (s, 1H), 7.56 (d, 2H, J=8.8 Hz), 7.48 (d, 4H, J=7.9 Hz), 7.42–7.29 (m, 6H), 7.21 (d, 1H, J=7.0 Hz), 7.13 (d, 2H, J=8.8 Hz), 7.08 (d, 1H, J=2.2 Hz), 6.94 (dd, 1H, J=8.8, 2.4 Hz), 5.16 (s, 2H), 5.11 (s, 2H), 2.33 (s, 3H); IR (KBr) 3470, 2880, 2820, 1620 cm$^{-1}$; MS eI m/z 419.

EXAMPLE 2

5-Benzyloxy-2-(4-benzyloxy-phenyl)-3-methyl)-1-ylmethyl-(4-phenyliodide)-indole

A solution of the compound of Example 1 (3.0 g, 7.4 mmol) in DMF (25 mL) was treated with NaH (60% dispersion, 0.21 g, 8.9 mmol) and stirred at rt for 15 minutes. 4-iodobromobenzyl bromide (2.2 g, 7.4 mmol) was added and the reaction was stirred for 1 hour. The reaction mixture was poured into water and extracted with EtOAc, dried over MgSO$_4$ and concentrated. Trituration of the crude product with ether afforded 2.2 g of the product as a white solid: Mpt=153°–156° C.; $^1$H NMR (DMSO) 7.54 (d, 2H, J=8.6 Hz), 7.52–7.45 (m, 4H), 7.37–7.29 (m, 6H), 7.27 (d, 2H, J=8.8 Hz), 7.17 (d, 1H, J=9.0 Hz), 7.13 (d, 1H, J=2.2 Hz), 7.10 (d, 2H, J=8.8 Hz), 6.81 (dd, 1H, J=8.8, 2.4 Hz), 6.60 (d, 2H, J=8.3 Hz), 5.18 (s, 2H), 5.12 (s, 2H), 5.11 (s, 2H), 2.15 (s, 3H); MS eI m/z 635.

EXAMPLE 3

2-(4-hydroxyphenyl)-3-methyl)-1-ylmethyl-(4-phenyliodide)-indole-5-ol

A solution of the compound of Example 2 (2.2 g, 3.5 mmol) in CHCl$_3$ was treated with Iodotrimethylsilane (1.04 mL, 7.0 mmol) and the reaction was heated to reflux. After 2 h, an additional 3 eq of Iodotrimethylsilane was added and the reaction was stirred at rt for 18 h. The reaction was quenched by adding MeOH (5 mL). The organic layer was washed with an aqueous 10% solution of Na$_2$SO$_3$, HCl (1M) and dried over MgSO$_4$. The solution was concentrated and chromatographed on silica gel EtOAc/hexane (3:7) to yield 4a as a foam (1.2 g): $^1$H NMR 9.65 (s, 1H), 8.71 (s, 1H), 7.54 (d, 2H, J=8.3 Hz), 7.12 (d, 2H, J=8.3 Hz), 7.02 (d, 1H, J=8.6 Hz), 6.84–6.80 (m, 3H), 6.61 (d, 2H, J=8.3 Hz), 6.57 (dd, 1H, J=6.4 Hz), 5.12 (s, 2H), 2.09 (s, 3H); MS eI m/z 455.

General Procedure For Indole Propargylamine Preparation

The title compounds of Examples 4–6 were produced using a solution containing a 10 fold molar excess of a secondary amine in DMF cooled to 0° C. and treated with propargyl bromide (3 eq, 80% solution in toluene). After 1 h at 0° C., the reactions were allowed to rt for 1 h. The indole iodide (4a, 1 eq) was added followed by Cu(I)I (0.1 eq) and Pd(PPh$_3$)$_2$Cl$_2$ (0.035 eq). The reaction mixture was then stirred 16–48 h and worked up by pouring into water and extracting into EtOAc. The EtOAc is concentrated and chromatographed on silica gel using EtOAc/hexane as eluting system.

EXAMPLE 4

2-(4-Hydroxy-phenyl)-3-methyl-1-|4-(3-N,N-dimethyl-1-yl-prop-1-ynyl)-benzyl|-1H-indol-5-ol Mp=173°–176° C.; $^1$H NMR (DMSO) 9.64 (s, 1H), 8.70 (s, 1H), 7.25 (d, 2H, J=8.1 Hz), 7.12 (d, 2H, J=8.3 Hz), 7.03 (d, 1H, J=8.6 Hz), 6.83–6.78 (m, 5H), 6.57 (dd, 1H, J=8.8, 2.4 Hz), 5.17 (s, 2H), 3.39 (s, 2H), 2.19 (s, 6H), 2.10 (s, 3H); IR (KBr) 3390, 1490 cm$^{-1}$; MS esI 411 (M+H$^+$).

EXAMPLE 5

2-(4-Hydroxy-phenyl)-3-methyl-1-|4-(3-piperidin-1-yl-prop-1-ynyl)-benzyl|-1H-indol-5-ol Mp=118°–123° C.; $^1$H NMR (DMSO) 9.65 (s, 1H), 8.71 (s, 1H), 7.24 (d, 2H, J=8.1 Hz), 7.12 (d, 2H, J=8.6 Hz), 7.02 (d, 1H, J=8.6 Hz), 6.83–6.80 (m, 5H), 6.57 (dd, 1H, J=8.6, 2.2 Hz), 5.17 (s, 2H), 3.39 (s, 2H), 2.41 (m, 4H), 2.10 (s, 3H), 1.48 (p, 4H, J=5.7 Hz), 1.36–1.33 (m, 2H); IR (KBr) 3400, 2920, 1620, 1420 cm$^{-1}$; MS EI m/z 450; CHN calc'd for C$_{30}$H$_{30}$N$_2$O$_2$+0.25 H$_2$O.

EXAMPLE 6

2-(4-Hydroxy-phenyl)-3-methyl-1-|4-(3-pyrrolidin-1-yl-prop-1-ynyl)-benzyl|-1H-indol-5-ol (5c)

Mp=174°–176° C.; 1H NMR (DMSO) 9.64 (s, 1H), 8.70 (s, 1H), 7.23 (d, 2H, J=8.3 Hz), 7.11 (d, 2H, J=8.6 Hz), 7.02 (d, 1H, J=8.8 Hz), 6.84 (m, 5H), 6.57 (dd, 1H, J=8.6, 2.2 Hz), 5.17 (s, 2H), 3.53 (s, 2H), 2.53–2.51 (m, 4H), 2.09 (s, 3H), 1.69–1.66 (m, 4H); IR (KBr) 3400, 2920, 2900, 1620 cm$^{-1}$; MS eI m/z 436; CHN calcd for C$_{29}$H$_{28}$N$_2$O$_2$+0.7 H$_2$O.

In vitro estrogen receptor binding assay
Receptor preparation

CHO cells overexpressing the estrogen receptor were grown in 150 mm$^2$ dishes in DMEM+10% dextran coated charcoal, stripped fetal bovine serum. The plates were washed twice with PBS and once with 10 mM Tris-HCl, pH 7.4, 1 mM EDTA. Cells were harvested by scraping the surface and then the cell suspension was placed on ice. Cells were disrupted with a hand-held motorized tissue grinder using two, 10-second bursts. The crude preparation was centrifuged at 12,000 g for 20 minutes followed by a 60 minute spin at 100,000 g to produce a ribosome free cytosol. The cytosol was then frozen and stored at −80° C. Protein concentration of the cytosol was estimated using the BCA assay with reference standard protein.

Binding assay conditions

The competition assay was performed in a 96-well plate (polystyrene*) which binds <2.0% of the total input |$^3$H|-17β-estradiol and each data point was gathered in triplicate. 100 uG/100 uL of the receptor preparation was aliquoted per well. A saturating dose of 2.5 nM |$^3$H|17β-estradiol+ competitor (or buffer) in a 50 uL volume was added in the preliminary competition when 100× and 500×0 competitor were evaluated, only 0.8 nM |$^3$H| 17β-estradiol was used. The plate was incubated at room temperature for 2.5 h. At the end of this incubation period 150 uL of ice-cold dextran coated charcoal (5% activated charcoal coated with 0.05% 69K dextran) was added to each well and the plate was immediately centrifuged at 99 g for 5 minutes at 4° C. 200 uL of the supernatant solution was then removed for scintillation counting. Samples were counted to 2% or 10 minutes, whichever occurs first. Because polystyrene absorbs a small amount of |$^3$H|17β-estradiol, wells containing radioactivity and cytosol, but not processed with charcoal were included to quantitate amounts of available isotope. Also, wells containing radioactivity but no cytosol were processed with charcoal to estimate unremovable DPM of |$^3$H| 17β-estradiol. Corning #25880-96, 96-well plates were used because they have proven to bind the least amount of estradiol.

Analysis of results

Counts per minute (CPM) of radioactivity were automatically converted to disintegrated per minute (DPM) by the Beckman LS 7500 Scintillation Counter using a set of quenched standards to generate a H# for each sample. To calculate the % of estradiol binding in the presence of 100 or fold 500 fold competitor the following formula was applied:

((DPM sample-DPM not removed by charcoal/(DPM estradiol-DPM not removed by charcoal))×100%=% of estradiol binding For the generation of IC$_{50}$ curves, % binding is plotted vs compound. IC$_{50}$'s are generated for compounds that show >30% competition at 500× competitor concentration. For a description of these methods, see Hulme, E. C., ed. 1992. Receptor-Ligand Interactions: A Practical Approach. IRL Press, New York. (see especially chapter 8).

Estrogen Receptor Affinity (reported as RBA: 17β-estradiol=100)

| Compound | RBA |
| --- | --- |
| Raloxifene | 400 |
| Tamoxifen | 1.8 |
| Example 4 | 53 |
| Example 5 | 23 |

Ishikawa Cell Alkaline Phosphatase Assay
Cell Maintenance and Treatment

Ishikawa cells were maintained in DMEM/F12 (50%:50%) containing phenol red+10% fetal bovine serum and the medium was supplemented with 2 mM Glutamax, 1% Pen/Strap and 1 mM sodium pyruvate. Five days prior to the beginning of each experiment (treatment of cells) the medium was changed to phenol red-free DMEM/F12+10% dextran coated charcoal stripped serum. On the day before treatment, cells were harvested using 0.5% trypsin/EDTA and plated at a density of 5×10$^4$ cells/well in 96-well tissue culture plates. Test compounds were dosed at 10$^{-6}$, 10$^{-7}$ and 10$^{-8}$M in addition to 10$^{-6}$M (compound)+10$^{-9}$M 17β-estradiol to evaluate the ability of the compounds to function as antiestrogens. Cells were treated for 48 h prior to assay. Each 96-well plate contained a 17β-estradiol control. Sample population for at each dose was n=8.

Alkaline Phosphatase Assay

At the end of 48 h the media is aspirated and cells are washed three times with phosphate buffered saline (PBS). 50 μL of lysis buffer (0.1M Tris-HCl, pH 9.8, 0.2% Triton X-100) is added to each well. Plates are placed at −80° C. for a minimum of 15 minutes. Plates are thawed at 37° C.

followed by the addition of 150 μL of 0.1M Tris-HCl, pH 9.8, containing 4 mM para-nitrophenylphosphate (pNPP) to each well (final concentration, 3 mM pNPP).

Absorbance and slope calculations were made using the KineticCalc Application program (Bio-Tek Instruments, Inc., Winooski, Vt.). Results are expressed as the mean±S.D. of the rate of enzyme reaction (slope) averaged over the linear portion of the kinetic reaction curve (optical density readings every 5 minutes for 30 minutes absorbance reading). Results for compounds are summarized as percent of response related to 1 nM 17β-estradiol.

Various compounds were assayed for estrogenic activity by the alkaline phosphatase method and corresponding ED50 values (95% C.I.) were calculated. The four listed in the following were used as as reference standards:

| | |
|---|---|
| 17β-estradiol | 0.03 nM |
| 17α-estradiol | 1.42 nM |
| estriol | 0.13 nM |
| estrone | 0.36 nM |

A description of these methods is described by Holinka, C. F., Hata, H., Kuramoto, H. and Gurpide, E. (1986) Effects of steroid hormones and antisteroids on alkaline phosphatase activity in human endometrial cancer cells (Ishikawa Line). Cancer Research, 46:2771–2774, and by Littlefield, B. A., Gurpide, E., Markiewicz, L., McKinley, B. and Hochberg, R. B. (1990) A simple and sensitive microtiter plate estrogen bioassay based on stimulation alkaline phosphatase in Ishikawa cells; Estrogen action of D5 adrenal steroids. Endocrinology, 6:2757–2762.

Ishikawa Alkaline Phosshatase Assay

| Compound | % Activation | % Activation (Compound + 1 nM 17β-estradiol) |
|---|---|---|
| 17β-estradiol | 100% | N/A |
| tamoxifen | 0% | 45% |
| raloxifen | 5% | 5% |
| Example 4 | 34% | 34% |
| Example 5 | 27% | 23% |

2X VIT ERE Transfection Assay
Cell Maintenance and Treatment

Chinese Hamster Ovary cells (CHO) which had been stably transfected with the human estrogen receptor were maintained in DMEM+10% fetal bovine serum (FBS). 48 h prior to treatment the growth medium was replaced with DMEM lacking phenol red+10% dextran coated charcoal stripped FBS (treatment medium). Cells were plated at a density of 5000 cells/well in 96-well plates containing 200 μL of medium/well.

Calcium Phoshate Transfection

Reporter DNA (Promega plasmid pGL2 containing two tandem copies of the vitellogenin ERE in front of the minimal thymidine kinase promoter driving the luciferase gene) was combined with the B-galactosidase expression plasmid pCH110 (Pharmacia) and carrier DNA (pTZ18U) in the following ratio:

10 uG of reporter DNA
5 uG of pCH110DNA
5 uG of pTZ18U
20 uG of DNA/1 mL of transfection solution The DNA (20 uG) was dissolved in 500 uL of 250 mM sterile $CaCl_2$ and added dropwise to 500 uL of 2×HeBS (0.28M NaCl, 50 mM HEPES, 1.5 mM $Na_2HPO_4$, pH 7.05) and incubated at room temperature for 20 minutes. 20 uL of this mixture was added to each well of cells and remained on the cells for 16 h. At the end of this incubation the precipitate was removed, the cells were washed with media, fresh treatment media was replaced and the cells were treated with either vehicle, 1 nM 17β-estradiol, 1 uM compound or 1 uM compound+1 nM 17β-estradiol (tests for estrogen antagonism). Each treatment condition was performed on 8 wells (n=8) which were incubated for 24 h prior to the luciferase assay.

Luciferase Assay

After 24 h exposure to compounds, the media was removed and each well washed with 2× with 125 uL of PBS lacking $Mg^{++}$ and $Ca^{++}$. After removing the PBS, 25 uL of Promega lysis buffer was added to each well and allowed to stand at room temperature for 15 min, followed by 15 min at −80° C. and 15 min at 37° C. 20 uL of lysate was transferred to an opaque 96 well plate for luciferase activity evaluation and the remaining lysate (5 uL) was used for the B-galactosidase activity evaluation (normalize transfection). The luciferan substrate (Promega) was added in 100 uL aliquots to each well automatically by the luminometer and the light produced (relative light units) was read 10 seconds after addition.

Infection Luciferase Assay

| Compound | % Activation | % Activation with 1 nM 17β-estradiol |
|---|---|---|
| 17β-estradiol | 100% | N/A |
| tamoxifen | 0% | 10% |
| raloxifene | 0% | 0% |
| Example 4 | 34% | 34% |
| Example 5 | 17% | 19% |

B-Galactosidase Assay

To the remaining 5 uL of lysate 45 uL of PBS was added. Then 50 uL of Promega B-galactosidase 2× assay buffer was added, mixed well and incubated at 37° C. for 1 hour. A plate containing a standard curve (0.1 to 1.5 miliunits in triplicate) was set up for each experimental run. The plates were analyzed on a Molecular Devices spectrophotometric plate reader at 410 nm. The optical densities for the unknown were converted to milliunits of activity by mathematical extrapolation from the standard curve.

Analysis of Results

The luciferase data was generated as relative light units (RLUs) accumulated during a 10 second measurement and automatically transferred to a JMP (SAS Inc) file where background RLUs were subtracted. The B-galactosidase values were automatically imported into the file and these values were divided into the RLUs to normalize the data. The mean and standard deviations were determined from a n=8 for each treatment. Compounds activity was compared to 17β-estradiol for each plate. Percentage of activity as compared to 17β-estradiol was calculated using the formula %=((Estradiol-control)/(compound value))×100. These techniques are described by Tzukerman, M. T., Esty, A., Santiso-Mere, D., Danielian, P., Parker, M. G., Stein, R. B., Pike, J. W. and McDonnel, D. P. (1994). Human estrogen receptor transactivational capacity was determined by both cellular and promoter context and mediated by two functionally distinct intramolecular regions (see Molecular Endocrinology, 8:21–30).

Rat Uterotrophic/Antiuterotrophic Bioassay

The estrogenic and antiestrogenic properties of the compounds were determined in an immature rat uterotrophic assay (4 day) that (as described previously by L. J. Black and R. L. Goode, Life Sciences, 26, 1453 (1980)). Immature Sprague-Dawley rats (female, 18 days old) were tested in groups of six. The animals were treated by daily ip injection with 10 uG compound, 100 uG compound, (100 uG compound+1 uG 17β-estradiol) to check antiestrogenicity, and 1 uG 17β-estradiol, with 50% DMSO/50% saline as the injection vehicle. On day 4 the animals were sacrificed by $CO_2$ asphyxiation and their uteri were removed and stripped of excess lipid, any fluid removed and the wet weight determined. A small section of one horn was submitted for histology and the remainder used to isolate total RNA in order to evaluate complement component 3 gene expression.

4 day Ovariectomized Rat Model

| Compound | 10 μG | 100 μG | |
|---|---|---|---|
| Tamoxifen | 69.6 mg | 71.4 mg | |
| Raloxifen | 47.5 | 43.2 | |
| control = 42.7 mg | | 1 μG 17β-estradiol = 98.2 | |

| Compound | 10 μG | 100 μG | 100 μG + 1 μG 17β-estradiol |
|---|---|---|---|
| Example 4 | 56.0 mg | 84.0 mg | 77.6 mg |
| control = 32.1 mg | | 1 μG 17β-estradiol = 90.2 mg | |
| Example 5 | 55.6 mg | 71.3 mg | 66.8 mg |
| control = 21.7 mg | | 1 μg 17β-estradiol = 82.8 mg | |

What is claimed:

1. A compound having the structure:

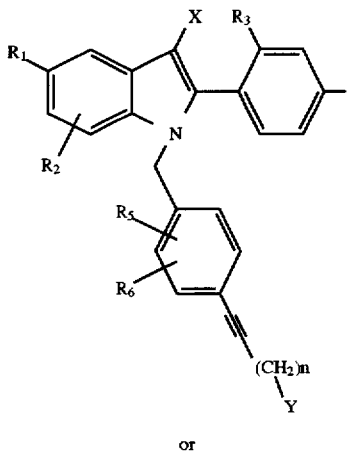

or

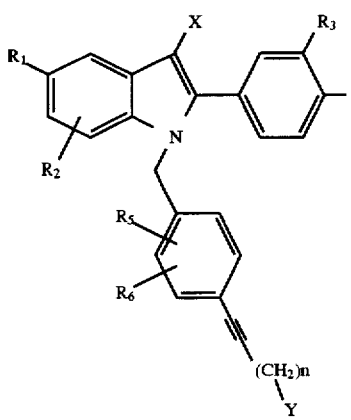

wherein:

$R_1$ is selected from H, OH, the $C_1$–$C_4$ esters or alkyl ethers thereof or halogen;

$R_2$, $R_3$, $R_4$, $R_5$, and $R_6$ are independently selected from H, OH or the $C_1$–$C_4$ esters or alkyl ethers thereof, halogen, cyano, $C_1$–$C_6$ alkyl, or trifluoromethyl, with the proviso that, when $R_1$ is H, $R_2$ is not OH;

X is selected from H, $C_1$–$C_6$ alkyl, cyano, nitro, trifluoromethyl, or halogen;

n is 2 or 3;

Y is selected from:

a) the moiety:

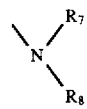

wherein $R_7$ and $R_8$ are independently selected from the group of H, $C_1$–$C_6$ alkyl, phenyl; or b) a five-membered saturated, unsaturated or partially unsaturated heterocycle containing up to two heteroatoms selected from the group consisting of —O—, —NH—, —N($C_1C_4$ alkyl)-, —N=, and —S(O)$_m$—, wherein m is an integer of from 0–2, optionally substituted with 1–3 substituents independently selected from the group consisting of hydrogen, hydroxyl, halo, $C_1$–$C_4$ alkyl, trihalomethyl, $C_1$–$C_4$ alkoxy, trihalomethoxy, $C_1$–$C_4$ acyloxy, $C_1$–$C_4$ alkylthio, $C_1$–$C_4$ alkylsulfinyl, $C_1$–$C_4$ alkylsulfonyl, hydroxy ($C_1$–$C_4$)alkyl, phenyl optionally substituted with 1–3 ($C_1$–$C_4$)alkyl, —$CO_2H$—, —CN, —CONHR$^1$, —$NH_2$, $C_1$–$C_4$ alkylamino, $C_1$–$C_4$ dialkylamino, —$NHSO_2R^1$—, —NHCOR$^1$—, —$NO_2$—;

or a pharmaceutically acceptable salt thereof.

2. A compound of claim 1 having the structure:

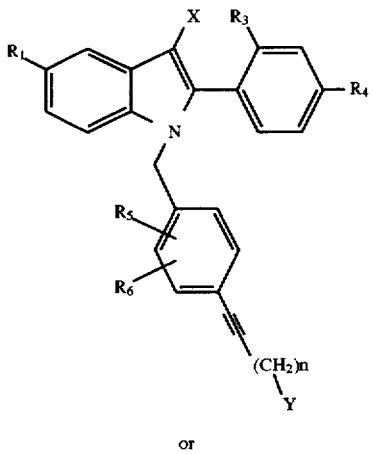

or

-continued

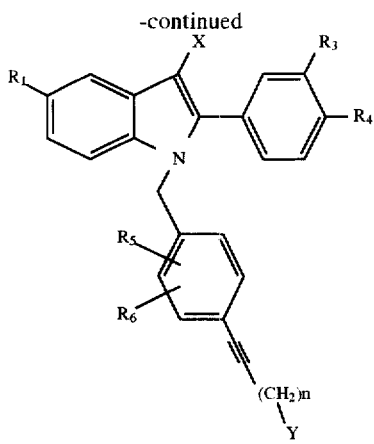

wherein:

$R_1$ is selected from OH, the $C_1$–$C_4$ esters or alkyl ethers thereof, or halogen;

$R_3$, $R_4$, $R_5$, and $R_6$ are independently selected from H, OH or the $C_1$–$C_4$ esters or alkyl ethers thereof, halogen, cyano, $C_1$–$C_6$ alkyl, or trifluoromethyl, with the proviso that, when $R_1$ is H, $R_2$ is not OH;

X is selected from H, $C_1$–$C_6$ alkyl, cyano, nitro, trifluoromethyl, or halogen;

n is 2 or 3;

Y is selected from:
a) the moiety:

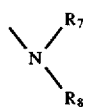

wherein $R_7$ and $R_8$ are independently selected from the group of H, $C_1$–$C_6$ alkyl, phenyl; or b) a five-membered saturated, unsaturated or partially unsaturated heterocycle containing up to two heteroatoms selected from the group consisting of —O—, —NH—, —N($C_1C_4$ alkyl)-, —N=, and —S(O)$_m$—, wherein m is an integer of from 0–2, optionally substituted with 1–3 substituents independently selected from the group consisting of hydrogen, hydroxyl, halo, $C_1$–$C_4$ alkyl, trihalomethyl, $C_1$–$C_4$ alkoxy, trihalomethoxy, $C_1$–$C_4$ acyloxy, $C_1$–$C_4$ alkylthio, $C_1$–$C_4$ alkylsulfinyl, $C_1$–$C_4$ alkylsulfonyl, hydroxy ($C_1$–$C_4$)alkyl, phenyl optionally substituted with 1–3 ($C_1$–$C_4$)alkyl, —CO$_2$H—, —CN—, —CONHR$^1$—, —NH$_2$—, $C_1$–$C_4$ alkylamino, $C_1$–$C_4$ dialkylamino, —NHSO$_2$R$^1$, —NHCOR$^1$, —NO$_2$—;

or a pharmaceutically acceptable salt thereof.

3. A compound of claim 1 which is 2-(4-Hydroxyphenyl)-3-methyl-1-|4-(3-N,N-dimethyl-1-yl-prop-1-ynyl)-benzyl|-1H-indol-5-ol or a pharmaceutically acceptable salt thereof.

4. A compound of claim 1 which is 2-(4-Hydroxyphenyl)-3-methyl-1-|4-(3-pyrrolidin-1-yl-prop-1-ynyl)-benzyl|-1H-indol-5-ol or a pharmaceutically acceptable salt thereof.

5. A pharmaceutical composition comprising a compound of claim 1, or a pharmaceutically acceptable salt thereof, and a pharmaceutically acceptable carrier or excipient.

6. The pharmaceutical composition of claim 5 in which the compound is 2-(4-Hydroxy-phenyl)-3-methyl-1-|4-(3-N,N-dimethyl-1-yl-prop-1-ynyl)-benzyl|-1H-indol-5-ol or a pharmaceutically acceptable salt thereof.

7. The pharmaceutical composition of claim 5 in which the compound is 2-(4-Hydroxy-phenyl)-3-methyl-1-|4-(3-pyrrolidin-1-yl-prop-1-ynyl)-benzyl|-1H-indol-5-ol or a pharmaceutically acceptable salt thereof.

8. A method of treating or preventing bone loss in a mammal, the method comprising administering to a mammal in need thereof an effective amount of a compound of claim 1, or a pharmaceutically acceptable salt thereof.

9. A method of treating or preventing disease states or syndromes which are caused or associated with an estrogen deficiency in a mammal, the method comprising administering to a mammal in need thereof an effective amount of a compound of claim 1, or a pharmaceutically acceptable salt thereof.

10. A method of treating or preventing cardiovascular disease in a mammal, the method comprising administering to a mammal in need thereof an effective amount of a compound of claim 1, or a pharmaceutically acceptable salt thereof.

* * * * *